US009919298B2

(12) United States Patent
Schmidt et al.

(10) Patent No.: US 9,919,298 B2
(45) Date of Patent: *Mar. 20, 2018

(54) CATALYST COMPOSITIONS FOR SELECTIVE DIMERIZATION OF ETHYLENE

(71) Applicant: SAUDI BASIC INDUSTRIES CORPORATION, Riyadh (SA)

(72) Inventors: Roland Schmidt, Wiehl (DE); Mohammed H. Al-Hazmi, Riyadh (SA); Mohammed F. Al-Anazi, Riyadh (SA); DevRanjan J. Pradhan, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/102,768

(22) PCT Filed: Dec. 12, 2014

(86) PCT No.: PCT/IB2014/066864
§ 371 (c)(1),
(2) Date: Jun. 8, 2016

(87) PCT Pub. No.: WO2015/087304
PCT Pub. Date: Jun. 18, 2015

(65) Prior Publication Data
US 2017/0001182 A1   Jan. 5, 2017

Related U.S. Application Data

(60) Provisional application No. 61/915,764, filed on Dec. 13, 2013, provisional application No. 61/916,549, filed on Dec. 16, 2013.

(51) Int. Cl.
| | | |
|---|---|---|
| C07C 2/30 | (2006.01) |
| C07C 11/02 | (2006.01) |
| B01J 31/02 | (2006.01) |
| B01J 31/14 | (2006.01) |
| C08F 110/02 | (2006.01) |
| C08F 10/00 | (2006.01) |
| C08F 10/08 | (2006.01) |

(52) U.S. Cl.
CPC .......... *B01J 31/0212* (2013.01); *B01J 31/02* (2013.01); *B01J 31/0204* (2013.01); *B01J 31/0231* (2013.01); *B01J 31/0237* (2013.01); *B01J 31/0274* (2013.01); *B01J 31/0275* (2013.01); *B01J 31/143* (2013.01); *C07C 2/30* (2013.01); *C08F 10/00* (2013.01); *C08F 10/08* (2013.01); *C08F 110/02* (2013.01); *B01J 2231/122* (2013.01); *B01J 2231/20* (2013.01); *B01J 2531/004* (2013.01); *B01J 2531/007* (2013.01); *C07C 2531/02* (2013.01); *C07C 2531/12* (2013.01); *C07C 2531/14* (2013.01)

(58) Field of Classification Search
CPC ......... C07C 2/30; C07C 2/26; C07C 2531/38; C07C 2531/14
See application file for complete search history.

(56) References Cited

U.S. PATENT DOCUMENTS

| | | | |
|---|---|---|---|
| 2,943,125 A | 6/1960 | Ziegler et al. | |
| 2,953,552 A | 9/1960 | Stampa et al. | |
| 3,911,042 A * | 10/1975 | Belov | C07C 2/30 585/512 |
| 3,969,429 A * | 7/1976 | Belov | C07C 2/30 585/512 |
| 4,101,600 A * | 7/1978 | Zhukov | B01J 31/0212 585/512 |
| 4,133,944 A * | 1/1979 | Cooper | C08F 10/02 526/104 |
| 4,532,370 A | 7/1985 | Le Quan et al. | |
| 4,615,998 A * | 10/1986 | Le Quan | B01J 31/0212 502/126 |
| 4,704,376 A * | 11/1987 | Blenkers | C08F 10/02 502/104 |
| 4,739,022 A | 4/1988 | Blenkers et al. | |
| 4,861,846 A * | 8/1989 | Cann | C08F 210/16 502/118 |

(Continued)

FOREIGN PATENT DOCUMENTS

| | | |
|---|---|---|
| CN | 87100132 A | 9/1987 |
| CN | 101199943 A | 6/2008 |

(Continued)

OTHER PUBLICATIONS

Chen et al., "Cocatalysts for Metal-Catalyzed Olefin Polymerization: Activators, Activation Processes, and Structure-Activity Relationships," Chemical Reviews, American Chemical Society, US, vol. 100, Jan. 1, 2000; pp. 1391-1434; XP007920121, [ISSN: 0009-2665, DOI: 10.1021 / CR980462J, retrieved on Mar. 28, 2000; pp. 1394, 1395.

Dixon et al., "Advances in Selective Ethylene Trimerisation—A Critical Overview," Journal of Organometallic Chemistry, Elsevier, vol. 689, No. 23, Nov. 15, 2004, pp. 3641-3668, XP004629409, ISSN: 0022-328X, DOI: 10.1016/J. Jorganchem, Jun. 8, 2004; pp. 3656-3657.

International Preliminary Report on Patentability and Written Opinion of the International Searching Authority for PCT/IB/2014/066865; International Filing Date—Dec. 12, 2014; dated Jun. 14, 2016; 7 pages.

International Preliminary Report on Patentability for International and Written Opinion, Application No. PCT/IB2014/066864; International Filing Date Dec. 12, 2014; dated Jun. 23, 2016; 17 pages.

(Continued)

*Primary Examiner* — Rip A Lee
(74) *Attorney, Agent, or Firm* — Cantor Colburn LLP

(57) ABSTRACT

A catalyst composition comprises an inert hydrocarbon solvent, having dissolved therein a titanate of the formula Ti(OR)$_4$ wherein each R is the same or different, and is a hydrocarbon residue, and an organic aluminum compound, wherein a molar ratio of the organic aluminum compound and any alkene present in the catalyst composition is greater than one.

18 Claims, 7 Drawing Sheets

(56) References Cited

U.S. PATENT DOCUMENTS

| | | | | |
|---|---|---|---|---|
| 5,030,790 A * | 7/1991 | Sergienko | ............... | C07C 2/30 585/512 |
| 5,043,514 A * | 8/1991 | McDaniel | ............... | B01J 21/08 526/119 |
| 5,877,376 A * | 3/1999 | Commereuc | ............ | C07C 2/30 585/512 |
| 9,499,455 B2 * | 11/2016 | Magna | ..................... | C07C 2/30 |
| 2005/0085376 A1 | 4/2005 | Nagy et al. | | |
| 2011/0288308 A1 | 11/2011 | Grasset et al. | | |
| 2013/0303817 A1 | 11/2013 | Shaik et al. | | |
| 2016/0310936 A1 | 10/2016 | Schmidt et al. | | |
| 2017/0007994 A1 * | 1/2017 | Lucciulli | ............. | B01J 31/0204 |

FOREIGN PATENT DOCUMENTS

| | | | | |
|---|---|---|---|---|
| EA | 009358 B1 | 12/2007 | | |
| EA | 014758 B1 | 2/2011 | | |
| EP | 0114416 | 8/1984 | | |
| EP | 0183604 A1 | 6/1986 | | |
| EP | 221 206 A1 * | 5/1987 | ............ | C07C 11/08 |
| EP | 0221206 A1 | 5/1987 | | |
| GB | 2 223 501 A * | 4/1990 | ............ | C08F 210/02 |
| RU | 2015726 C1 | 7/1994 | | |
| RU | 2429216 C2 | 9/2011 | | |
| WO | 2015118462 A1 | 8/2015 | | |

OTHER PUBLICATIONS

International Preliminary Report on Patentability for International Application No. PCT/IB2014/066863; International Filing Date—Dec. 12, 2014 and Written Opinion of the International Searching Authority, dated Jun. 14, 2016; 13 pages.

International Search Report and the Written Opinion for PCT/IB2014/066865, International Filing Date—Dec. 12, 2014; dated Jun. 17, 2015; 6 pages.

International Search Report and Written Opinion for International Application No. PCT/IB2014/066863; International Filing Date—Dec. 12, 2014; dated Sep. 12, 2015; 18 pages.

International Search Report and Written Opinion, International Application No. PCT/IB2014/066864, International Filing Date—Dec. 12, 2014; dated Sep. 29, 2015; 25 pages.

Invitation to Pay Additional Fees for International Application No. PCT/IB2014/066863, International Filing Date—Dec. 12, 2014, dated Jun. 25, 2015; 7 pages.

Invitation to Pay Additional Fees in International Application No. PCT/IB2014/066864; International Filing Date—Dec. 12, 2014; dated Jul. 16, 2015; 12 pages.

Sahgal et al., "Ethylene Solubility and Diffusivity in Hexane-Dodecane and Ethylene Glycol-Butanol Solutions," Journal of Chemical & Engineering Data, vol. 24, No. 3; Jul. 1, 1979, pp. 222-227, XP055195339, ISSN; 0021-9568, DOI: 10.1021/je60082a020.

Chinese Office Action for application No. 201480068195.1 dated Apr. 5, 2017 (8 pages).

European Search Report for application No. 17151294.0-1370 dated May 22, 2017, 7 pages.

Translation of Russian Office Action for application No. 2016122655 dated Jun. 1, 2017, 9 pages.

Translation of Russian Office Action for application No. 2016122656 dated Jun. 1, 2017, 11 pages.

Russian Office Action for application No. 2016122234 dated Jul. 27, 2017, 11 pages.

Chinese Office Action for application No. 201480067885.5 dated Sep. 1, 2017, 8 pages.

Chinese Office Action for application No. 201480063330.0 dated Dec. 5, 2017 (6 pages).

Gulf Co-Operation Council Office Action for Application No. GC 2014-28542 dated Oct. 9, 2017.

Gulf Co-Operation Council Office Action for Application No. GC 2014-28543 dated Oct. 11, 2017.

Office Action for Application No. GC 2014-28541 dated Oct. 9, 2017.

* cited by examiner

CATALYST COMPOSITIONS FOR SELECTIVE DIMERIZATION OF ETHYLENE

CROSS REFERENCE TO RELATED APPLICATIONS

This application is a National Stage application of PCT/IB2014/066864, filed Dec. 12, 2014, which claims the benefit of U.S. Provisional Application No. 61/915,764, filed Dec. 13, 2013, and U.S. Provisional Application No. 61/916,549, filed Dec. 16, 2013, both of which are incorporated by reference in their entirety herein.

FIELD

Disclosed herein are catalyst systems and processes for the dimerization of alkenes to prepare α-olefins, in particular catalyst systems and processes for the dimerization of ethylene to prepare 1-butene or downstream products thereof.

BACKGROUND

Alpha-olefins such as butene are desirable substances in the chemical industry. Due to the presence of the terminal double bond, they can be converted into a number of other valuable compounds. For example, butene can be converted to compounds such as butanol, butadiene, and butanone. In polymerisation reactions it can be used as monomer or co-monomer and is particularly valuable in the production of plastics. For example, it can be used as a co-monomer with ethylene for the production of high strength and high stress crack resistant polyethylenes. One route to the preparation of butene is the cracking of higher petrochemical fractions containing more than 4 carbon atoms. Another route to the preparation of butene, which has for a long time been the subject of intense research, is via the dimerization of ethylene (ethene). An aim of the catalytic dimerization of ethylene into 1-butene was producing higher chain polymers via the growth reaction of the organoaluminum compounds. The industrial synthesis of 1-butene can be achieved using nickel or titanium catalysts such as Alphabutol™ (Handbook of Petroleum Processing, Edited by D. S. J. Jones, P. R. Pujadó; Springer Science 2008; Forestière et al., Oil & Gas Science and Technology-Rev. IFP (2009); 64(6):649-667). The Alphabutol™ process is also known as BUCAT. The catalytic activity of Alphabutol™ can be low, at roughly 1 kg of product per gram of titanium. Polymer formation and lengthy initial induction period are major drawbacks for the commercial Alphabutol™ system.

Thus, a demand still remains in the art for improved processes for the preparation of α-olefins such as butene from alkenes such as ethene, especially for processes with one or more of long catalyst lifetimes, high specificity, short initiation times (induction periods), and reduced polymer formation.

SUMMARY

A catalyst composition comprises an inert hydrocarbon solvent, having dissolved therein a titanate of the formula Ti(OR)$_4$ wherein each R is the same or different, and is a hydrocarbon residue, and an organic aluminum compound, wherein a molar ratio of the organic aluminum compound and any alkene present in the catalyst composition is greater than one.

A process for the preparation of a catalyst composition comprises combining the components of the catalyst composition, preferably pre-treating the titanate by dissolving the titanate and optionally the catalyst modifier in the inert hydrocarbon solvent in the absence of the organic aluminum compound, preferably wherein not more than 0.1% alkene is present in the catalyst composition during the process.

A process for the preparation of an α-olefin comprises contacting an alkene with the catalyst composition in a liquid phase and under conditions effective to form the α-olefin.

A process for the preparation of a downstream product comprises reacting the α-olefin as described above to provide the downstream product, preferably wherein the downstream product is a homopolymer or copolymer comprising units derived from the α-olefin.

BRIEF DESCRIPTION OF THE DRAWINGS

The following Figures are intended for illustration only and are not to be considered as limiting the scope.

DETAILED DESCRIPTION

Figure 1:
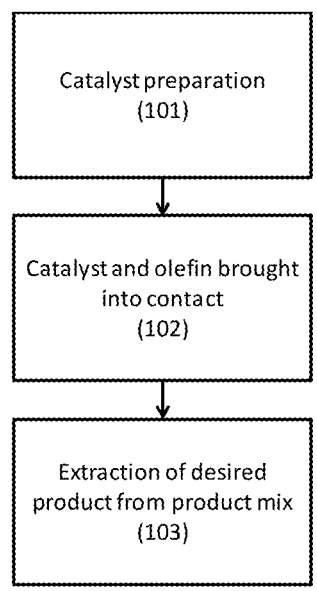
FIG. 1 represents a schematic process for producing olefin in accordance with one example of the presently disclosed subject matter.

The present invention is generally based on the object of overcoming at least one of the problems encountered in the state of the art in relation to the dimerization reaction of an alkene, preferably ethene, to give an α-olefin, preferably 1-butene, or downstream products derived therefrom, preferably polymers.

In some embodiments, the present invention is further based on the object of providing a catalyst system and a process for a reaction that has one or more, preferably all, of a high product specificity, reduced polymer fouling, and a high catalyst lifetime.

In some embodiments, the present invention is based on the object of providing a catalyst system and a process for a reaction which has a short initiation time.

Another object is to provide an efficient and sustainable α-olefin source for producing downstream products and shaped bodies.

A contribution to achieving at least one of the above-mentioned objects is made by a catalyst composition comprising the following catalyst components:

a. a titanate of formula Ti(OR)$_4$ wherein each R is the same or different and is a hydrocarbon residue, preferably an alkyl group or an aryl group, more preferably an alkyl group;

b. a catalyst additive, wherein the catalyst additive is a dibutyl ether, a silicate, a silazane, an aromatic ether, a fluorocarbon, or a combination comprising at least one of the foregoing; and c. an organic aluminium compound.

Another contribution to achieving at least one of the above-mentioned objects is made by a catalyst composition comprising the following catalyst components:
   a. a titanate with the general formula Ti(OR)$_4$, wherein R is a hydrocarbon residue and each R can be the same as or different to the other R in the molecule;
   b. an organic aluminium compound; and
   c. a hydrocarbon,
wherein the catalyst components are dissolved in the hydrocarbon c; and wherein the molar ratio of the amount of aluminium compound b. to the total amount of alkene is greater than one. A catalyst additive as described above or a catalyst modifier may be present in this embodiment, where the catalyst additive may be a a dibutyl ether, a silicate, a silazane, an aromatic ether, a fluorocarbon, or a combination comprising at least one of the foregoing; or an amine or ether catalyst modifier distinct from the dibutyl ether or the aromatic ether as further described below; or a combination comprising at least one of the foregoing.

Another contribution to achieving at least one of the above mentioned objects, is made by a process for the preparation of a catalyst composition comprising the following preparation steps:
   a. providing a hydrocarbon;
   b. introducing a titanate with the general formula Ti(OR)$_4$, wherein R is a hydrocarbon residue and each R can be the same as or different to the other R in the molecule, into the hydrocarbon; and
   c. introducing an aluminium compound into the hydrocarbon,
wherein not more than 0.1% alkene is present in the catalyst composition during any of the steps a, b, or c. In some embodiment the process further comprises a cooling step. Another aspect is a catalyst composition obtainable by this process. In this embodiment, a preferred catalyst composition comprises the following:
   a. a tetraalkyl titanate, preferably tetra-n-butyl titanate;
   b. an ether catalyst modifier, preferably tetrahydrofuran;
   c. a trialkyl aluminium compound, preferably triethyl aluminium; and
   d. an alkane, preferably hexane.

Preferred titanates are compounds of the general formula Ti(OR)$_4$, wherein R stands for a hydrocarbon residue, preferably an alkyl group or an aryl group, more preferably an alkyl group, and each R in a molecule may be the same as or different to the other R groups in the molecule. Titanates are known to the skilled person, and the specific titanate may be selected in order to enhance the advantageous properties of the process. R is preferably a straight chain or branched alkyl group, more preferably straight chain. R is preferably a $C_2$-$C_{12}$ alkyl group, more preferably a $C_2$-$C_8$ alkyl group, most preferably a $C_3$-$C_5$ alkyl group. The preferred alkyl group is butyl, which includes n-butyl and iso-butyl. Suitable organic titanium compounds include, but are not limited to, tetraethyl titanate, tetraisopropyl titanate, titanium tetra-n-butoxide (TNBT), and tetra-2-ethylhexyl titanate. In one embodiment, the organic titanium compound is titanium tetra-n-butoxide.

In some embodiments, the titanate can be present in high concentration in the reaction mixture, for example in a concentration of about 0.0001 to about 0.1 mol/dm$^3$, about 0.0002 to about 0.01 mol/dm$^3$, more preferably about 0.0005 to about 0.001 mol/dm$^3$.

The organic aluminum compound is usually compounds of the formula AlR$_3$, wherein R stands for a hydrocarbon, hydrogen or a halogen, preferably a hydrocarbon or a halogen, more preferably alkyl or aryl or halogen, most preferably an alkyl group or halogen and each R in a molecule may be the same as or different to the other R groups in the molecule. Aluminium compounds are known to the skilled person, wherein specific aluminium compounds are selected in order to enhance the advantageous properties of the process. R is preferably a straight chain or branched alkyl group, more preferably straight chain. R is preferably a $C_1$-$C_{12}$ alkyl group, more preferably a $C_1$-$C_8$ alkyl group, most preferably a $C_1$-$C_4$ alkyl group. The preferred alkyl group is ethyl. Suitable organic aluminum compounds include, but are not limited to, triethylaluminum (TEAL), tripropylaluminum, triisobutylaluminum, diisobutylaluminum hydride, and trihexylaluminum. In one embodiment, the organic aluminum compound is triethylaluminum.

The molar ratio of Al:Ti of the catalyst composition can impact the catalytic activity of the catalyst composition. In one example, the catalytic activity can be enhanced when the Al:Ti molar ratio is increased, as shown in Example 1. In addition, when the catalyst composition is used for producing 1-butene via catalytic dimerization of ethylene, the Al:Ti molar ratio can impact the polymer (e.g., polyethylene) formation during the production process, as shown in Example 1. In one example, increased Al:Ti molar ratio can lead to higher polymer formation. The Al:Ti molar ratio of the catalyst composition can range from about 1:1 to about 40:1, from about 1:to about 30:1, from about 1:1 to about 20:1, from about 1:1 to about 10:1, from about 1:1 to about 6:1, from about 1:1 to about 5:1, from about 1:1 to about 4:1, from about 1:1 to about 3:1, from about 1:1 to about 2:1, from about 2:1 to about 5:1, from about 2:1 to about 3:1, from about 3:1 to about 4:1 or from about 4:1 to about 5:1 In certain embodiments, the Al:Ti molar ratio of the catalyst composition is from about 1:to about 5:1. The polymer formation can be avoided when the Al:Ti molar ratio is about 5:1 or less, as shown in Example 1. In some embodiments, the Al:Ti molar ratio of the catalyst composition is about 5:1. In some embodiments, the Al:Ti molar ratio of the catalyst composition is about 3:1. In other embodiments, the Al:Ti molar ratio of the catalyst composition is about 2:1.

The catalyst additive may be a dibutyl ether, a silicate, a silazane, an aromatic ether, a fluorocarbon, or a combination comprising at least one of the foregoing. As used herein the term "catalyst additive" is used for convenience to refer to one or more of the foregoing compounds, and is not intended to imply any particular functional or mechanistic properties of the compounds.

In some embodiments, the catalyst additive comprises dibutyl ether, specifically di-n-butyl ether, di-iso-butyl ether, or a combination comprising at least one of the foregoing.

In some embodiments the catalyst additive comprises a silicate, where the silicate has the formula SiR$_y$(OR)$_{4-y}$, wherein y is 0 to 3, preferably wherein y is 0, and each R is the same or different and is hydrogen or a $C_{1-12}$ hydrocarbon residue, preferably $C_1$-$C_6$ alkyl group, provided that R is not hydrogen when it is directly bonded to silicon.

In some embodiments the silicate has the general formula Si(OR)$_4$ or SiR$_x$(OR)$_{4-x}$ with x=1, 2 or 3, wherein R stands for a hydrocarbon residue or H, preferably an alkyl group or an aryl group, most preferably an alkyl group; and each R in the molecule may be the same as or different to the other R in the molecule. In some embodiments of the catalyst composition, at least one R group of the silicate is a $C_1$-$C_{12}$ alkyl group, preferably a $C_1$-$C_6$ alkyl group, more preferably a $C_1$-$C_3$ alkyl group. In an aspect of this embodiment, all of the R groups in the silicate are alkyl groups, the same as or different to each other, in the range $C_1$-$C_{12}$, preferably in the range $C_1$-$C_6$, more preferably in the range $C_1$-$C_3$. In preferred embodiments of the catalyst composition, the silicate is $Si(OEt)_4$, that is, $Si(OCH_2CH_3)_4$.

In some embodiments, the silicate has the general formula $Si(OR)_4$. In an aspect of this embodiment, the silicate is $Si(OC_2H_5)_4$.

In some embodiments, the silicate has the general formula $SiR_x(OR)_{4-x}$. In the aspects of this embodiment, the silicate has the formula $SiR(OR)_3$, $SiR_2(OR)_2$, $SiR_3(OR)$. In an aspect of this invention, all R in the silicate are ethyl, the silicate having a formula selected from the group consisting of the following: $Si(C_2H_5)(OC_2H_5)_3$, $Si(C_2H_5)_2(OC_2H_5)_2$, and $Si(C_2H_5)_3(OC_2H_5)$.

In some embodiments the catalyst additive comprises a silazane. Preferred silazanes have the general formula $(SiR_3)NH(SiR_3)$, wherein R is a hydrocarbon, H, or a halogen, and each R may be the same as or different to the other R in the molecule. Preferred hydrocarbons R in this context are methyl, ethyl, propyl, butyl, phenyl, toluyl, or cyclohexyl, preferably methyl. Preferred halogens in this context are F, Cl, Br, or I, preferably Cl or F, preferably F. In some embodiments, the catalyst composition comprises $(Si(CH_3)_3)_2NH$.

In some embodiments the catalyst additive comprises an aromatic ether of the formula $R^1OR^2$, wherein each $R^1$ is a hydrocarbon residue and $R^2$ is an aromatic hydrocarbon residue, preferably wherein each $R^1$ and $R^2$ is the same or different substituted or unsubstituted $C_{6-15}$ aromatic group, more preferably wherein each $R^1$ and $R^2$ is the same substituted or unsubstituted $C_{6-10}$ aromatic group, most preferably wherein each $R^1$ and $R^2$ is phenyl. Preferred aromatic ethers comprising an aromatic hydrocarbon are methyl phenyl ether, ethyl phenyl ether, propyl phenyl ether, butyl phenyl ether, cyclohexyl phenyl ether, and preferably diphenyl ether.

In some embodiments the catalyst additive comprises a fluoro hydrocarbon. In some embodiments preferred fluoro hydrocarbons in this context are mono- di- tri- or tetra-fluorinated hydrocarbons, based on methane, ethane, propane, butane, benzene, toluene, naphthalene, or xylene, preferably based on benzene. In some embodiments the fluoro hydrocarbon is a fluorinated $C_{1-15}$ hydrocarbon, preferably a fluorinated $C_{6-12}$ aromatic hydrocarbon, more preferably fluorobenzene. The fluorinated $C_{1-15}$ hydrocarbon may be mono- di- tri- or tetra- fluorinated, or have more fluorine substituents, and may be perfluorinated.

In some embodiments, it is preferred for the catalyst composition to comprise a catalyst modifier, in particular an amine catalyst modifier or an ether catalyst modifier that is distinct from the dibutyl ether and the aromatic ether.

Such ether catalyst modifiers are known, and can act as a co-catalyst or catalyst modifiers to the titanate, preferably by coordination of the titanate with a lone pair of electrons. Such ether catalyst modifiers are well known to the skilled person and he may select any ether which he considers to be appropriate in the context and preferably improving the favourable characteristics of the reaction, preferably a reduced initiation time, increased yield and reduced polymer fouling.

Preferred ether catalyst modifiers may be monoethers or polyethers. Preferred substituents of the ether are alkyl groups. Preferred alkyl groups are methyl, ethyl, propyl, n-butyl, iso-butyl, t-butyl, and other higher alkyl groups. Some preferred monoether catalyst modifiers are dimethyl ether, diethyl ether, dipropyl ether, dibutyl ether, methyl ethyl ether, methyl propyl ether, methyl butyl ether, ethyl propyl ether, ethyl butyl ether, propyl butyl ether, tetrahydrofuran, or dihydropyran. The preferred mono ether is tetrahydrofuran.

Preferred polyether catalyst modifiers are 1,4 dioxane or ethers based on polyalcohols, preferably glycols or glycerols, preferably ethylene glycol. Preferred ethers based on glycol are dimethyl ethylene glycol, diethyl ethylene glycol, dipropyl ethylene glycol, dibutyl ethylene glycol, methyl ethyl ethylene glycol, methyl propyl ethylene glycol, methyl butyl ethylene glycol, ethyl propyl ethylene glycol, ethyl butyl ethylene glycol, propyl butyl ethylene glycol.

In some embodiments, the catalyst composition contains the dibutyl ether modifier or the aromatic ether modifier and one further ether catalyst modifier distinct from the dibutyl ether and the aromatic ether, preferably an ether as described above, more preferably tetrahydrofuran.

In another embodiment, the catalyst composition contains the butyl ether modifier two or more further ether catalyst modifiers distinct from the dibutyl ether and the aromatic ether, preferably with at least one or more, preferably all, as described above, preferably with one of the ethers being tetrahydrofuran.

In some embodiments the catalyst additive and the further ether catalyst modifier are present in a molar ratio in the range of about 1:5 to about 5:1, preferably in the range from about 1:3 to about 3:1, more preferably in the range from about 1:2 to about 2:1. In an aspect of this embodiment, the dibutyl ether and the further ether catalyst modifier are present in the catalyst composition in a molar ratio in the range of about 1:5 to about 5:1, preferably in the range from about 1:3 to about 3:1, more preferably in the range from about 1:2 to about 2:1.

As previously stated, in some embodiments a dibutyl ether, a silicate, a silazane, an aromatic ether, or a fluoro-carbon catalyst additive is not present. In these embodiments the amine or ether catalyst modifier distinct from the dibutyl ether and the aromatic ether as described above can be present, however. In an embodiment an ether catalyst modifier is present, and tetrahydrofuran is preferred. In another embodiment, the catalyst composition contains at least two or more ether catalyst modifiers, preferably with at least one or more, preferably all, as described above, preferably with one of the ethers being tetrahydrofuran.

The skilled person may modify the relative ratios of the components of the catalyst composition in order to increase the advantageous properties of the reaction.

The catalyst compositions catalyse the reaction of an alkene, preferably ethene, to obtain an $\alpha$-olefin, preferably 1-butene. It is preferred that the catalyst composition contribute to favourable properties of the reaction, preferably to improved catalyst activity, product selectivity of $\alpha$-olefin and reduction of undesired polymer fouling. Preferred catalyst compositions comprise a tetra($C_{1-4}$)alkyl titanate, more preferably a tetra-n-butyl titanate; a catalyst additive that can be dibutyl ether, a combination of dibutyl ether and tetrahydrofuran, a silicate, a fluoro hydrocarbon, an aromatic ether, a silazane; and triethyl aluminium. Other preferred catalyst compositions comprise a tetra($C_{1-4}$)alkyl titanate, more preferably a tetra-n-butyl titanate; optionally, an ether catalyst modifier, preferably tetrahydrofuran, an inert hydrocarbon, preferably hexane; and triethyl aluminium.

The catalyst composition may be present dissolved in a liquid, preferably an alkane, preferably hexane, preferably as a homogeneous liquid. In an aspect of this embodiment, the liquid is an alkane or an alkene or an aromatic solvent. In a further aspect of this embodiment, the liquid is a $C_4$-$C_{12}$ alkane, preferably a $C_4$-$C_8$, more preferably a $C_4$-$C_6$ alkane;

or a $C_4$-$C_{12}$ alkene, preferably a $C_4$-$C_8$ alkene, more preferably a $C_4$-$C_6$ alkene. In a further aspect of this embodiment, the liquid is one or more selected from the group consisting of butene, hexane, heptane, and octane.

The catalyst composition may be pre-prepared or prepared in situ, and preferably is pre-prepared.

When prepared in situ, the components of the catalyst composition are introduced to the reaction system as two or more components that are added sequentially.

In some embodiments, the titanate is pre-mixed with an ether catalyst modifier, optionally together with the catalyst additive. In an aspect of this embodiment, they are mixed in an inert solvent, preferably an alkane, preferably one or more of the following: pentane, hexane, heptane, octane, nonane, or decane, preferably hexane.

In some embodiments, the titanate, the ether catalyst modifier, optional catalyst additive, or a combination thereof, and the organic aluminium compound are premixed, preferably in the absence of an olefin (alkene). In an aspect of this embodiment, they are mixed in an inert solvent, preferably an alkane, preferably one or more of pentane, hexane, heptane, octane, nonane, or decane, preferably hexane.

It was found that certain solvents (e.g., olefins) can render the organic aluminum compound unavailable from activating the organic compound of titanium. In addition, certain solvents (e.g., olefins) can lead to increased induction period. The presently disclosed processes of making the catalyst compositions include pre-treating the organic titanium compound with an inert solvent, and adding the organic aluminum compound to the mixture of the organic titanium compound and the inert solvent to activate the organic titanium compound in the presence of the inert solvent. Furthermore, the organic titanium compound can be dissolved in or mixed with an ether prior to or concurrently at the inert solvent pre-treating procedure. In one embodiment, the catalyst can be mixed with the ether prior to the inert solvent pre-treating. Thus, in some embodiments, the titanate is pre-mixed with a catalyst modifier, preferably an ether catalyst modifier, preferably tetrahydrofuran. In an aspect of this embodiment, they are mixed in an inert solvent, preferably an alkane, preferably one or more selected from the group consisting of the following: pentane, hexane, heptane, octane, nonane, decane, preferably hexane. It has been unexpectedly found that this pre-treatment process can result in shortened initiation times. The catalyst additive can further be optionally mixed at the same time as the titanate and the ether catalyst modifier.

Pre-treating the organic titanium compound with an inert solvent (e.g., n-hexane) can provide a condition for the subsequently added organic aluminum compound to pre-activate the organic titanium compound prior to adding the catalyst composition that includes the organic titanium compound and the organic aluminum compound to the solvent, which, as presented above, can render the organic aluminum compound unavailable from activating the organic titanium compound. The pre-activation of the organic titanium compound can yield a controlled catalyst reaction, and can also shorten the induction period, as described in Example 2. Once the organic titanium compound is activated in the pre-activation procedure, it can remain active. The pre-treating can be conducted in a nitrogen atmosphere.

Figure 3:
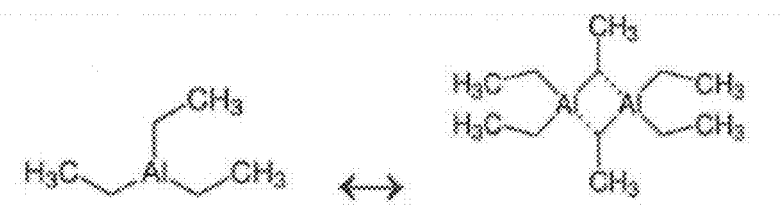
FIG. 3 represents two forms of triethylaluminum.
Figure 4:
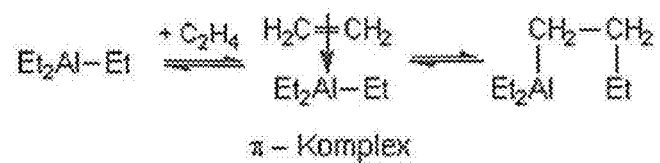
FIG. 4 illustrates an "Aufbaureaktion" or ring opening reaction.

In accordance with the presently disclosed subject matter, the organic aluminum compound can be TEAL. TEAL can exist in two forms: monomeric form ($AlEt_3$) and dimeric form ($Al_2Et_6$), where Et is ethyl, $CH_2CH_3$, as shown in FIG. 3. In the presence of the ether that dissolves the catalyst (e.g., THF), TEAL remains in the monomeric form. The catalytic activity of TEAL accelerates when it exists in the monomeric form. Therefore, in the presence of the ether that dissolves the catalyst (e.g., THF), TEAL exists in the monomeric form that enables it to activate the catalyst, e.g., TNBT. In the presence of certain solvents, such as olefins (e.g., 1-hexene), TEAL remains in the dimeric form, which renders TEAL unable to activate the catalyst, e.g., TNBT. Furthermore, certain solvents, such as olefins (e.g., 1-hexene) are associated with other side reactions, for example, the so-called "Aufbaureaktion" or ring opening reactions as described in Delaney et. al., J. Chem. Soc. Perkin Trans (1986); Rosenthal et. al., Organometallics (2007); 26:3000-3004, and as shown in FIG. 4. The "Aufbaureaktion" or ring opening reactions can render the co-catalyst and/or catalyst unavailable for important catalyst reduction to the active form.

In other embodiments, the titanate, the ether catalyst modifier, and the aluminium compound are premixed, preferably in the absence of olefin. In one aspect of this embodiment, they are mixed in an inert solvent, preferably an alkane, preferably one or more selected from the group consisting of the following: pentane, hexane, heptane, octane, nonane, decane, preferably hexane. The catalyst additive can further be optionally mixed at the same time with these components in the inert solvent.

In some embodiments, the preparation of the catalyst composition comprises the following steps:
1. First, the titanate, preferably the titanate and ether catalyst modifier, are premixed in an inert solvent, preferably an alkane, preferably one or more selected from the group consisting of the following: pentane, hexane, heptane, octane, nonane, decane, preferably hexane.
2. Second, the aluminium compound is introduced into the inert solvent.

In still other embodiments, a process to form the catalyst includes combining the organic aluminum compound and the inert solvent to provide an organic aluminum solution; and combining the organic aluminum solution with the titanate and optionally the catalyst modifier. The inert solvent is preferably an alkane, preferably one or more selected from the group consisting of the following: pentane, hexane, heptane, octane, nonane, decane, preferably hexane. The catalyst additive can further be optionally mixed at the same time with the titanated in the inert solvent.

In some embodiments, no more than 10% of alkene is present in the preparation of the catalyst compositions. Preferably, no alkene is present in any of the steps of the catalyst preparation. The catalyst composition first comes into contact with alkene during the reaction for the preparation of the α-olefin. In some embodiments, no polymer is present or created in the catalyst composition during its preparation.

In some embodiments, the catalyst composition is prepared shortly before use in the preparation of an α-olefin. It is preferred for the prepared catalyst system not be stored for longer than 1 week, preferably not longer than 1 day, more preferably not longer than 5 hours before being employed as catalyst for the preparation of an α-olefin or other reaction process.

In some embodiments, the catalyst composition is not activated until shortly before being employed in the reaction. It is preferred that the organic aluminium compound not be brought into contact with the other catalyst components earlier than 30 minutes, preferably not earlier than 15 minutes, more preferably not earlier than 10 minutes, most preferably not earlier than 5 minutes before the catalyst composition is employed in the reaction.

In some embodiments it is preferred for the individual components to be prepared shortly before use. It is preferred that at least one or more of the catalyst components not be stored for longer than 1 week, preferably not longer than 1 day, more preferably not longer than 5 hours after its preparation and before being employed as a component of the catalyst for the reaction. In an aspect of this embodiment, the titanate is not stored for longer than 1 week, preferably not longer than 1 day, more preferably not longer than 5 hours after its preparation and before being employed as a component of the catalyst in the reaction. In an aspect of this embodiment, the organic aluminium compound is not stored for longer than 1 week, preferably not longer than 1 day, more preferably not longer than 5 hours after its preparation and before being employed as a component of the catalyst for the reaction.

A contribution to achieving at least one of the above mentioned objects is made by a reaction process for the preparation of an α-olefin from an alkene, preferably a reaction process for preparation of a $C_4$-$C_{20}$ α-olefin from a $C_2$-$C_8$ alkene, most preferably a process for preparation of 1-butene from ethene. In some embodiments of a process for the preparation of the α-olefin, an alkene, preferably a $C_2$-$C_8$ alkene, most preferably ethene, comes into contact with a catalyst composition as described above. The α-olefin includes at least 2 repeat units based on the alkene. The alkene and the catalyst may come into contact in a homogeneous liquid phase.

In some embodiments, the reaction is carried out as a flow reaction. In other embodiments, the reaction is carried out as a batch reaction. It is preferred that the reaction proceed as a homogeneous liquid phase reaction.

FIG. 1 shows a schematic process diagram 100 for an example batch reaction process. In the first step 101 the catalyst is prepared. In the next or second step 102 the catalyst and olefin, preferably ethene, are brought into contact in the liquid phase, preferably in 1-butene as a solvent. In the subsequent or third step 103 the α-olefin product of the reaction, preferably 1-butene, is separated from the product mix. Optionally, the catalyst can be salvaged from the product mix. The catalyst can thus be recycled.

Figure 2:
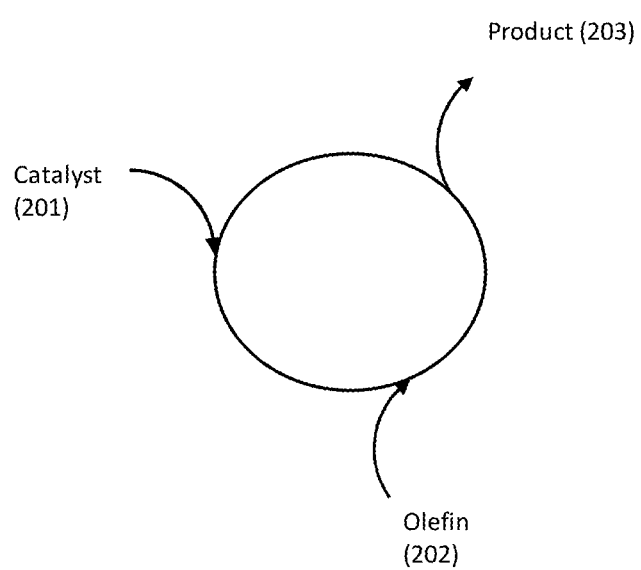
FIG. 2 represents a schematic process for producing olefin in accordance with one example of the presently disclosed subject matter.

FIG. 2 shows a schematic process diagram 200 for an example flow reaction process. In the first step 201 the catalyst is prepared and introduced into the reaction system, preferably a 1-butene solvent system. The catalyst components can either be premixed or added sequentially. In the second step 202 the alkene, preferably ethene, is introduced into the reaction system. In the third step 203 the α-olefin product, preferably 1-butene, is removed from the reaction system.

The skilled person can select the solvent for the reaction process in order to improve the advantageous properties of the reaction. The solvent for the reaction is preferably an alkane, an alkene, or an aromatic hydrocarbon. Preferred alkanes in this context are $C_2$-$C_{12}$ alkanes, preferably $C_4$-$C_8$ alkanes, most preferably hexane, heptane, or octane, including all isomers of each, and more preferably n-hexane. Preferred alkenes in this context are $C_2$-$C_{12}$ alkenes, preferably $C_4$-$C_8$ alkenes, including all isomers of each, most preferably butene. Preferred aromatic hydrocarbons in this context are benzene, toluene, and phenol.

In some embodiments, the preferred solvent for the reaction is the same as the α-olefin product, preferably 1-butene.

In other embodiments, the solvent for the reaction is different than the solvent employed for preparation of the catalyst system.

The reaction can be performed at a temperature of from about 20° C. to about 150° C., from about 40° C. to about 100° C., from about 20° C. to about 70° C., from about 50° C. to about 70° C., from about 50° C. to about 55° C., or from about 55° C. to about 65° C. In one embodiment, the reaction is performed at a temperature of about 60° C. The reaction can be performed at a pressure of from about 5 bars to about 50 bars, from about 10 bars to about 40 bars, or from about 15 bars to about 30 bars. In some embodiments, it is preferred that at least one of the following conditions be satisfied during the reaction:
 a. the pressure of the system is about 1 to about 50 bar, preferably about 5 to about 50 bar, more preferably about 10 to about 40 bar, most preferably in the range from about 15 to about 30 bar; or
 b. the temperature of the system is about 30 to about 150° C., preferably about 40 to about 100° C., more preferably about 50 to about 70° C., most preferably about 55 to about 65° C.

In some embodiments, the reaction is conducted in a batch where a selected volume of the presently disclosed catalyst composition can be introduced into a reactor provided with usual stirring and cooling systems, and can be subjected therein to an ethylene pressure, which can be from about 22 bars to about 27 bars. In some embodiments, the reaction using the presently disclosed catalyst composition is conducted at an ethylene pressure of about 23 bars. One of ordinary skill in the art can adjust the temperature, pressure and other conditions of the reaction in order to bring about favorable properties of the reaction, for example, in order to ensure that the reaction system is present as a homogeneous liquid phase.

The above conditions are particularly preferred where the solvent for the reaction is 1-butene, in order to ensure that the reaction system is present as a homogeneous liquid phase. Where other solvents are used, the skilled person may adjust the temperature, pressure and other conditions of the reaction in order to bring about favourable properties of the reaction and in order to ensure that the reaction system is present as a homogeneous liquid phase. In some embodiments of the process, the alkene and the catalyst come into contact in a liquid phase comprising at least 50 wt. % but-1-ene, based on the total weight of the liquid phase.

The reaction product may be extracted by any method which the skilled person considers to suitable in the context. Preferred methods of extraction include distillation, precipitation, crystallisation, membrane permeation, and the like.

In some embodiments, the reaction process for the preparation of an α-olefin is coupled to an further subsequent reaction in order to obtain a downstream product. Thus, a process for the preparation of a downstream product may comprise the following preparation steps:
 i. preparation of an α-olefin by a process according to the invention; and
 ii. reaction of the α-olefin to obtain the downstream product, for example a polymer.

Preferred downstream products are those obtained from polymerisation reactions, hydrogenation reactions, halogenation reactions, and other chemical functionalization reactions, preferably polymerisation reactions. Preferred monomeric downstream products are chlorobutene, butadiene, butanol, and butanone. Preferred functionalization products are aromatic or non-aromatic compounds, saturated or unsaturated compounds, ketones, aldehydes, esters, amides, amines, carboxylic acids, alcohols, and the like.

In some aspects, the polymer is a poly α-olefin or copolymer comprising at least one α-olefin as a co-monomer. Preferred polymerisation reactions can be mono-polymerization (i.e., homopolymerisation) reactions or copolymerization reactions, preferably copolymerization reactions. The preferred homopolymerisation product is polybutene. The preferred co-polymers comprise units derived from the α-olefin, preferably 1-butene, and one or more co-monomers such as ethene, propene, pentene, styrene, acrylic acid, methacrylic acid, methyl acrylate, methyl methacrylate, acrylonitrile, methacrylonitrile, or vinyl chloride, preferably ethene. The preferred copolymer is a copolymer of ethene and 1-butene, preferably with a larger weight percent (wt. %) of units derived from ethene monomers than of units derived from 1-butene monomers, preferably with a weight ratio of ethene units to 1-butene units of about 50:1 to about 5:1, more preferably about 30:1 to about 10:1, most preferably about 25:1 to about 15:1. The skilled person may vary the ratio relating the mass of ethene monomers and 1-butene monomers in order to achieve the desired properties of the copolymers, such as crystallinity and elasticity.

In some embodiments of the process for the preparation of a downstream product, the product contains compounds with chain lengths in proportions determined by or approximating to the Anderson Schulz Flory distribution.

In some embodiments, the downstream products are further connected to yield fatty acids, preferably with chain lengths in proportions determined by or approximating to the Anderson Schulz Flory distribution.

In some embodiments, the downstream products are further processed, particularly in the case where the downstream product is a polymer, particularly when it is a polybutene homopolymer or copolymer. In an aspect of this embodiment, this further processing preferably involves formation of shaped objects such as plastic parts for electronic devices, automobile parts, such as bumpers, dashboards, or other body parts, furniture, or other parts or merchandise, or for packaging, such as plastic bags, film, or containers.

The following examples are illustrative of the presently disclosed subject matter and they should not be considered as limiting the scope of the subject matter or claims.

EXAMPLES

The following test methods are applicable to the claims, and were used in the Examples.

Polymer fouling was identified by visual inspection and by using a metal spatula to scrape the inside surfaces of the reactor following completion of the reaction. Where polymer fouling occurs, a thin layer of polymer can be seen on the surfaces of the walls of the reactor and/or on the stirrer. The thin polymer layer is white is colour and includes thin strands.

Initiation time was determined by monitoring the pressure in the reactor or the flow rate of the feed to the reactor. Once the reaction starts, ethene feed is consumed.

In a batch reactor, onset of reaction is manifested as a drop in absolute pressure. Thus, pressure remains roughly constant during the initiation period and starts to drop once the initiation period is over. The initiation time is the time spent at roughly constant pressure once the reactants and catalyst have been brought into contact and before the reaction starts.

In a continuous reactor, onset of reaction is manifest as an increase in the flow rate of ethene entering the reactor. At constant pressure, there is roughly no flow of ethene into the reactor during the initiation period. Ethene flows into the reactor once the initiation period is over. The initiation time is the time spent at roughly zero flow rate once the reactants and catalyst have been brought into contact and before the reaction starts.

Example 1

Example 1 illustrates the catalyst system including a tetra-substituted titanate, a dibutyl ether, and trialkyl aluminium, and its use in a process for the preparation of an α-olefin from an alkene, in particular preparation of 1-butene from ethene. The results are summarized in Table 1.

Example 1a. The reaction is carried out in a batch reactor (Parr 300 ml Autoclave Model 4566 Mini Benchtop reactor) at 60° C. and 23 bar. This temperature and pressure ar maintained in the reactor throughout the reaction. 0.25 ml tetra-n-butyl titanate (Dorf KETAL) and 0.25 ml dibutyl ether (Aldrich) are introduced into 50 ml n-hexane (Aldrich). To this is added 1.8 ml 1M solution of triethyl aluminium in n-hexane. The catalyst system in hexane is introduced into the reactor. The reaction system is heated to 60° C. under stirring and pressured to 23 bar with ethene for 1 hour. The product is collected in an adjacent vessel after depressurising.

Example 1b (comparative). Example 1a is repeated except with 0.25 ml tetrahydrofuran in place of 0.25 ml dibutyl ether.

Example 1c. Example 1a is repeated except with a mixture of 0.125 ml tetrahydrofuran and 0.125 ml dibutyl ether in place of 0.25 ml dibutyl ether.

TABLE 1

| Example | Dibutyl ether (ml) | Tetrahydrofuran (ml) | Yield | Activation time |
|---------|--------------------|-----------------------|-----------|-----------------|
| 1a | 0.25 | 0 | High | Short |
| 1b | 0 | 0.25 | Medium | Medium |
| 1c | 0.125 | 0.125 | Very high | Very short |

Example 2

Example 2 illustrates the catalyst system comprising tetraalkyl titanate, a silicate, and trialkyl and its use in a process for the preparation of an α-olefin from an alkene, in particular preparation of 1-butene from ethene. The results are summarized in Table 2.

Example 2a. The reaction was carried out in a batch reactor (Parr 300 ml Autoclave Model 4566 Mini Benchtop reactor) at 60° C. and 23 bars. This temperature and pressure were maintained in the reactor throughout the reaction. 0.25 ml tetra-n-butyl titanate (Dorf KETAL) and 0.25 ml tetraethyl silicate (Aldrich) were introduced into 50 ml n-hexane (Aldrich). To this was added 1.8 ml 1M solution of triethyl aluminium in n-hexane. The catalyst system in hexane was introduced into the reactor. The reaction system was heated to 60° C. under stirring and pressured to 23 bar with ethene for 1 hour. The product was collected in an adjacent vessel after depressurising. The yield of 1-butene, expressed as the percentage based on full conversion of the introduced ethene, was 90%. No polymer fouling was observed.

Example 2b (comparative). Example 2a was repeated except with 9 ml tetrahydrofuran in place of 25 ml tetraethyl silicate. The observed yield was <1%. Some polymer fouling was observed.

TABLE 2

| Example | Co-catalyst | Yield | Polymer fouling |
|---|---|---|---|
| 2a | $Si(OCH_2CH_3)_4$ | 90% | No |
| 2b | Tetrahydrofuran | <1% | Yes |

Example 3

Example 3 illustrates the catalyst system comprising a titanate, an ether, a methyl aluminoxane, and optionally a second aluminum compound, and its use in a process for the preparation of an polymer from an alkene, in particular preparation of polyethylene from ethene.

Example 3a. The reaction was carried out in a batch reactor (Parr 300 ml Autoclave Model 4566 Mini Benchtop reactor) at 60° C. and 23 bar. This temperature and pressure were maintained in the reactor throughout the reaction. 0.25 ml tetra-n-butyl titanate (Dorf KETAL) and 0.25 ml tetrahydrofuran (Aldrich) were introduced into 50 ml n-hexane (Aldrich). To this was added 1.8 ml 1M solution of methyl aluminoxane in n-heptane (MAO). The catalyst system in hexane was introduced into the reactor. The reaction system was heated to 60° C. under stirring and pressured to 23 bar with ethene for 1 hour. The product was collected in an adjacent vessel after depressurising. The yield of polymer, expressed as the percentage based on full conversion of the introduced ethene, was 95%.

Example 3b. Example 3a was repeated except that 1.8 ml 1M solution of modified methyl aluminoxane $(CH_3)_{0.7}(iso-But)_{0.3}$ (MMAO) was employed in place of the methyl aluminoxane.

Example 3c. Example 3a was repeated except that a mixture of 0.9 ml 1M solution of methyl aluminoxane and 0.9 ml 1M triethyl aluminium (TEAL) was employed in place of the methyl aluminoxane.

Example 3d. Example 3a was repeated except that a mixture of 0.9 ml 1M solution of modified methyl aluminoxane $(CH_3)_{0.7}(iso-But)_{0.3}$ and 0.9 ml 1M triethyl aluminium was employed in place of the methyl aluminoxane.

Example 3e (Comparative). Example 3a was repeated except that 1.8 ml 1M solution of triethyl aluminium was employed in place of the methyl aluminoxane.

The results are summarized in Table 3, where results are ranked on a scale of 1 to 5, with 1 being the least favourable and 5 being the most favourable.

TABLE 3

| Example | Activator | Yield | Initiation time | Catalyst lifetime |
|---|---|---|---|---|
| 3a | MAO | 2 | 2 | 2 |
| 3b | MMAO | 3 | 3 | 3 |
| 3c | MAO and TEAL | 4 | 4 | 4 |
| 3d | MMAO and TEAL | 5 | 5 | 5 |
| 3e | TEAL | 1 | 1 | 1 |

Example 4

Example 4 illustrates the pre-mixed catalyst composition comprising a titanate and an aluminium compound, preferably trialkyl aluminium, and its use in a process for the preparation of an α-olefin from an alkene, in particular preparation of 1-butene from ethene.

Example 4a. 50 ml hex-1-ene (from Aldrich) was introduced into a batch reactor (Parr 300 ml Autoclave Model 4566 Mini Benchtop reactor) at 60° C. and 23 bar pressure of ethene. This temperature and pressure were maintained in the reactor throughout the reaction. 0.25 ml tetra-n-butyl titanate (Dorf KETAL) and 0.25 ml tetrahydrofuran (from Aldrich) were introduced into 50 ml n-hexane. 1.8 ml 1M solution of triethyl aluminium in n-hexane (Aldrich) was introduced into the hexane. The catalyst system in hexane was introduced into the reactor. The reaction system was heated to 60° C. under stirring and pressured to 23 bar with ethene for 1 hour. The product was collected in an adjacent vessel after depressurising. The yield of 1-butene and initiation time were determined.

Example 4b (Comparative). 50 ml 1-butene (from Aldrich) was introduced into a batch reactor (Parr 300 ml Autoclave Model 4566 Mini Benchtop reactor) at 60° C. and 23 bar pressure of ethene. This temperature and pressure were maintained in the reactor throughout the reaction. 0.25 ml tetra-n-butyl titanate (Dorf KETAL) and 0.25 ml tetrahydrofuran (Aldrich) were introduced into 50 ml n-hexane. Tetra-n-butyl titanate and tetrahydrofuran in hexane was introduced into the reactor. 1.8 ml 1M solution of triethyl aluminium in n-hexane (Aldrich) was introduced into the reactor. The reaction system was heated to 60° C. under stirring and pressured to 23 bar with ethene for 1 hour. The product was collected in an adjacent vessel after depressurising. The yield of but-1-ene and the initiation time were determined.

TABLE 4

| Example | Catalyst composition | Yield | Initiation time |
|---|---|---|---|
| 4a | Pre-mixed | High | Fast |
| 4b | sequential addition | Medium | Slow |

Example 5

Example 5 illustrates the catalyst system comprising a titanate, a catalyst modifier, and a methyl aluminoxane, and its use in a process for the preparation of an α-olefin from an alkene, in particular preparation of 1-butene from ethene. The results are summarized in Table 5.

Example 5a. The reaction is carried out in a batch reactor (Parr 300 ml Autoclave Model 4566 Mini Benchtop reactor) at 60° C. and 23 bar. This temperature and pressure are maintained in the reactor throughout the reaction. 0.25 ml tetra-n-butyl titanate (Dorf KETAL) and 0.25 ml of the catalyst modifier (Aldrich) are introduced into 50 ml n-hexane (Aldrich). To this is added 1.8 ml 1M solution of triethyl aluminium in n-hexane. The catalyst system in hexane is introduced into the reactor. The reaction system is heated to 60° C. under stirring and pressured to 23 bar with ethene for 1 hour. The product is collected in an adjacent vessel after depressurising.

Example 5b. Example 5a was repeated except that 0.25 ml of diphenylether was used in place of the silazane.

Example 5c. Example 5a was repeated except that 0.25 ml of fluorobenzene was used in place of the silazane.

Example 5d (Comparative). Example 5a was repeated except that 0.25 ml of tetrahydrofuran was used in place of the silazane.

TABLE 5

| Example | Catalyst modifier | Yield | Activation time | Polymer fouling |
|---|---|---|---|---|
| 5a | ((CH$_3$)$_3$Si)$_2$NH | Very high | Very short | No |
| 5b | Ph$_2$O | Very high | Very short | No |
| 5c | PhF | Very high | Very short | No |
| 5d | Tetrahydrofuran | Medium | Medium | No |

Example 6a

Al/Ti Ratio—Activity and Selectivity

Figure 5:
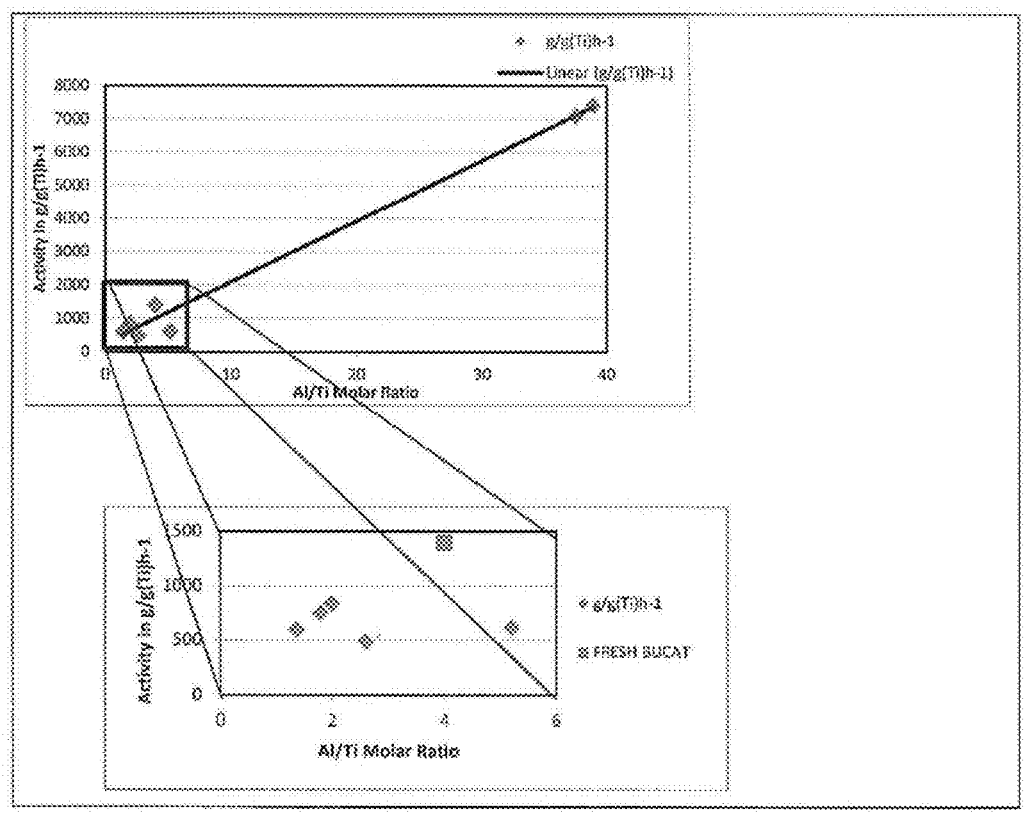
FIG. 5 illustrates the relationship of catalytic activity with Al/Ti molar ratio.
Figure 6:
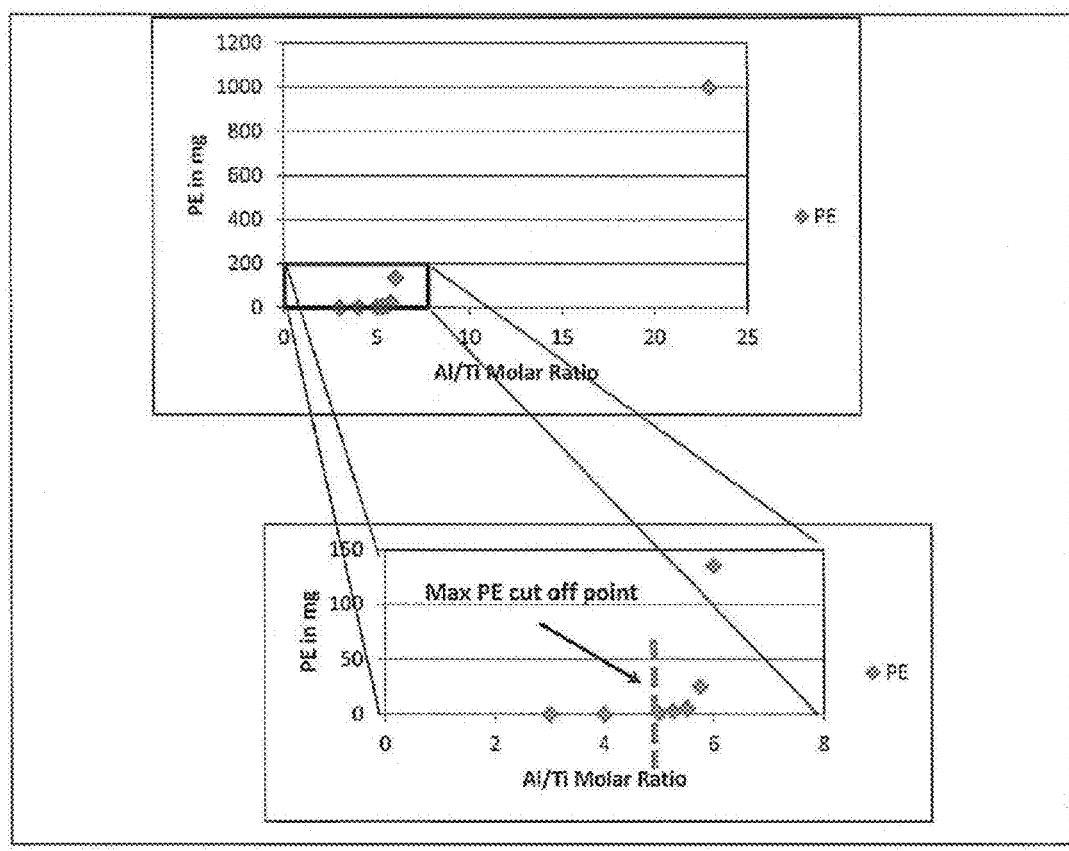
FIG. 6 illustrates the relationship of polymer formation with Al/Ti molar ratio.

It was found that the catalytic activity of a catalyst composition including TNBT as a catalyst and TEAL as a co-catalyst increased when the Al/Ti molar ratio was increased, as shown in FIG. 5. The 1-butene selectivity was unaffected within the margin of error (data not shown). While a higher Al/Ti molar ratio can lead to increased catalytic activity, it may also result in polymer formation, as shown in FIG. 6. It was found that the cut-off point of the Al/Ti molar ratio was about 5, above which, polymer formation was observed, as shown in FIG. 6.

Example 6b

Solvent Effect: The Role of 1-Olefins

Figure 7:
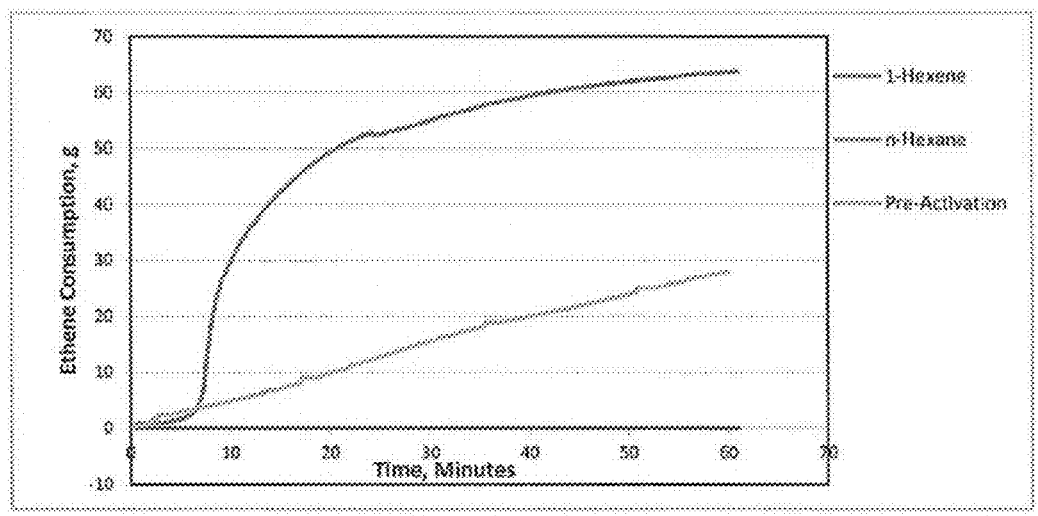
FIG. 7 illustrates the solvent effect on catalytic activity.

1-Hexene. The following experiments were conducted in a 300 ml jacketed Parr autoclave reactor (Parr Modell 4566). The standard conditions were 23 bars ethylene pressure and 60° C. for 1 hour. 1 ml of a catalyst solution that includes 45 vol. % THF and 55 vol % of TNBT where TNBT was not pre-treated with an inert solvent, was added to 50 ml of 1-hexene (from Aldrich), and 3.6 ml of TEAL was added prior to introduction into a batch reactor (e.g., an autoclave). No color change was observed; no visible TNBT activation was observed; and no reaction was observed, as shown in FIG. 7. Repeat experiments came to the same results, while there was a significant exotherm (heat release) observed once TEAL was added to 1-hexene. Accordingly, the solvent (e.g., olefins) can act as a co-catalyst poison impeding and rendering TEAL unavailable from activating the titanium complex.

n-Hexane. 1 ml of a catalytic solution including 45 vol. % THF and 55 vol % of TNBT was dissolved in 50 ml n-hexane prepared in a glove box under a nitrogen atmosphere. Prior to use, 3.6 ml of 1M TEAL solution was added (Al/Ti molar ratio is 3). Then, the mixture of TNBT/THF/TEAL/n-hexane was added to 25 ml n-hexane. The total ethylene consumption after 1 hour was 63.8 g. The induction period was about 3 minutes. The catalytic solution was added to the reactor by vacuum suction. The reactor was then pressurized with ethylene from a 2-liter aluminum gas cylinder (e ethylene supply) to reach the desired pressure (23 bars in most experiments). The reaction pressure was controlled using backpressure regulator, while the ethylene consumption was measured using a balance onto which the gas cylinder was placed. The reactor was equipped with a thermocouple to measure the temperature inside the reactor. Temperature, pressure, and ethylene consumption data were recorded using a data acquisition system. Prior to the catalyst/solvent injection, the reactor heated to 80° C. under vacuum for at least two hours under vacuum in order to eliminate all traces of moisture. The temperature was controlled by a heating mantle/furnace and cooling coil refrigeration. After terminating the reaction by depressurization, the product was collected, hydrolyzed with deionized water, and analyzed by GC and/or GC/MS. Total ethylene consumption was measured by weight difference of the attached ethylene storage cylinder.

The standard BUCAT catalyst batch tested for ethylene dimerization to 1-butene was evaluated under the following standard reaction conditions.

| | |
|---|---|
| Reaction Temperature | 60° C. |
| Ethylene Pressure | 23 bar |
| Al/Ti molar ratio | 2 |
| Ti loading in ZrX$_4$ | 1.5 mmol |
| Reaction Time | 1 hour |
| Agitator Speed | 600 rpm |
| n-Hexane amount | 50 ml |

The titanium concentration in standard BUCAT is 7.71 wt. %.

Pre-activation. 2 ml of TEAL and 5 ml of n-hexane were mixed in a small vial, and then 0.5 ml of a catalytic solution including 45 vol. % THF and 55 vol % of TNBT was added to the mixture of TEAL/n-hexane. A noticeable color change from clear to dark green was observed. In addition, immediate reduction was observed and no exotherm was observed. The mixture of TEAL/n-hexane/THF/TNBT was immediately added to 50 ml of 1-hexene. The color of the catalytic solution was changed from dark green to yellow. Subsequently, the mixture of TEAL/n-hexane/THF/TNBT/1-hexene was injected to an autoclave reactor by vacuum suction. Slow but immediate reaction was observed, which showed that the induction period was shortened, as shown in FIG. 7. The total ethylene consumption after 1 hour was about 28 g, as shown in FIG. 7. The pre-activation procedure (pre-activating TNBT by TEAL in the presence of n-hexane prior to introducing the catalyst composition to an olefin solvent, e.g., 1-hexene) yielded a controlled catalytic reaction, albeit at reduced activity. In addition, there was no fouling (precipitation of polyethylene) observed.

Example 6c

NMR Investigation of 1-Olefins Effect

To better understand the 1-olefins effect, various NMR experiments were conducted. In the presence of n-hexane, TEAL exists in the dimeric and monomeric form as AlEt$_3$ and Al$_2$Et$_6$ (see FIG. 3). The equilibrium mainly shifts towards the dimer. While the smaller trimethylaluminum (TMA) appears only as dimer, the larger the alkyl moiety gets the more the equilibrium shifts towards the monomeric form. In the presence of THF (or 1-hexene), polarity of the solvent increased resulting in a significant shift of $^1$H NMR signal to higher field, i.e., lower chemical shift (0.4 ppm to −1.0 ppm) forming a monomeric combined with the THF (AlR$_3$-THF adduct). Similarly, in presence of THF or 1-hexene, conversion of the dimeric into the monomeric form was evidenced by the observed chemical shifts of methyl- and methylene signals, i.e., from 0.3 ppm to-0.7 ppm & 1.0 ppm to 0.9 ppm, respectively.

$^{13}$C NMR studies showed only small differences in the signal pattern, except the variation of the methyl and methylene signal intensity of TEAL in the presence of THF. This observation supports the conversion of the dimeric into the monomeric species.

$^{27}$Al NMR studies also supported these observations and showed the formation of a 3-coordinated Al-complex (=monomer) as evidenced from the appearance of the $^{27}$Al signals at 183.0 ppm in presence of THF for both TMA and TEAL. On the other hand, the $^{27}$Al signals of TEAL/TMA appeared at 156.0 ppm (i.e., dimeric form with 4-coordinated Al-complex) in the absence of THF.

Consequently, the co-catalyst TEAL remained as a dimer in the presence of 1-hexene but the catalytic activity accelerates when the co-catalyst exists as a monomer. On the other hand, the co-catalyst TEAL/TMA converts into monomeric form in the presence of THF, thereby activating the catalyst.

The invention is further illustrated by the following embodiments.

Embodiment 1

A catalyst composition, comprising: an inert hydrocarbon solvent, having dissolved therein a titanate of the formula Ti(OR)$_4$ wherein each R is the same or different, and is a hydrocarbon residue, and an organic aluminum compound, wherein a molar ratio of the organic aluminum compound and any alkene present in the catalyst composition is greater than one.

Embodiment 2

The composition of embodiment 1, wherein the titanate is pre-treated with the inert hydrocarbon solvent in the absence of the aluminum compound.

Embodiment 3

The catalyst composition of embodiment 1, wherein the inert hydrocarbon solvent is an alkane or an aromatic hydrocarbon, preferably a $C_6$-$C_{12}$ alkane, most preferably n-hexane.

Embodiment 4

The catalyst composition of embodiment 1, wherein the ratio of aluminum to titanium in the catalyst composition is about 1:1 to about 40:1, preferably about 1:1 to about 5:1.

Embodiment 5

The catalyst composition of any one or more of the preceding embodiments, further comprising a catalyst modifier, preferably wherein the catalyst modifier is an amine, an ether, a silicate, a silazane, a fluorinated hydrocarbon, or a combination comprising at least one of the foregoing, preferably an ether, most preferably di-n-butyl ether, tetrahydrofuran, or a combination comprising at least one of the foregoing.

Embodiment 6

The catalyst composition according to any one or more of the preceding embodiments, wherein one or more of the following conditions is met: the content of compounds comprising a carbon chain of more than 20 carbon atoms is less than 0.1 wt. %, based on the total weight of the catalyst composition; or the content of a polymer comprising 5 or more repeat units is less than 0.1 wt. %, based on the total weight of the catalyst composition.

Embodiment 7

The catalyst composition according to any one or more of the preceding embodiments, wherein the titanate is Ti(O-butyl)$_4$, Ti(O-n-alkyl)$_4$, Ti(O-n-butyl)$_4$, or a combination comprising at least one of the foregoing; and the organic aluminium compound is of the formula Al$_n$R$_{3n}$, wherein n is 1 or 2 and each R is the same or different, and is hydrogen, a hydrocarbon residue, or halogen, preferably wherein the aluminium compound is triethyl aluminium.

Embodiment 8

A process for the preparation of a catalyst composition, comprising: combining the components of any one or more of embodiments to 1 to 7.

Embodiment 9

The process according to embodiment 8, comprising: pretreating the organic titanate, preferably the organic titanate, an ether catalyst modifier, and optionally the catalyst additive with the inert hydrocarbon solvent; and combining the pre-treated titanate with the organic aluminum compound.

Embodiment 10

The process of embodiment 8 or embodiment 9, wherein not more than 0.1% alkene is present in the catalyst composition during the process.

Embodiment 11

The process of embodiment 9 or embodiment 10, wherein the pre-treating the titanate comprises dissolving the titanate and optionally the catalyst modifier in the inert hydrocarbon solvent in the absence of the organic aluminum compound.

Embodiment 12

The process of embodiment 18, comprising: combining the organic aluminum compound and the hydrocarbon to provide an organic aluminum solution; and combining the organic aluminum solution with the titanate and optionally the catalyst modifier.

Embodiment 13

A catalyst composition made by the method of any one or more of the embodiments to 8 to 12.

Embodiment 14

A process for the preparation of an α-olefin, comprising contacting an alkene with the catalyst composition according to any one or more of the preceding embodiments in a liquid phase and under conditions effective to form the α-olefin.

Embodiment 15

The process of embodiment 14, wherein the alkene is ethene and the α-olefin is 1-butene.

Embodiment 16

The process of embodiment 14 or 15, wherein the contacting is in a homogeneous liquid phase.

Embodiment 17

The process of to any one or more of embodiments 1 to, wherein the liquid phase comprises the α-olefin, preferably wherein the liquid phase comprises at least about 50 wt. % 1-butene, based on the total weight of the liquid phase.

Embodiment 18

The process of any one or more of embodiments 14 to 17, wherein the conditions comprise at least one of a pressure of about 1 to about 120 bar, preferably about 5 to about 50 bar, or a temperature of about 30 to about 150° C., preferably about 40 to about 80° C.

Embodiment 19

A process for the preparation of a downstream product, the process comprising: reacting the α-olefin of any one or more of embodiments 1 to 18 to provide the downstream product, preferably wherein the downstream product is a homopolymer or copolymer comprising units derived from the α-olefin.

Embodiment 20

The process according to embodiment 19, further comprising shaping downstream product to provide an article.

The term "about" or "substantially" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value. The singular forms "a," "an," and "the" include plural referents unless the context clearly dictates otherwise. "Or" means "and/or." Unless defined otherwise, technical and scientific terms used herein have the same meaning as is commonly understood by one of skill in the art to which this invention belongs. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group.

All publications, patents, and patent applications cited herein are hereby expressly incorporated by reference for all purposes to the same extent as if each was so individually denoted.

Although the presently disclosed subject matter and its advantages have been described in detail, it should be understood that various changes, substitutions, and alterations can be made herein without departing from the spirit and scope of the presently disclosed subject matter as defined by the appended claims. Moreover, the scope of the presently disclosed subject matter is not intended to be limited to the particular embodiments described in the specification. Accordingly, the appended claims are intended to include within their scope such modifications.

We claim:

1. A catalyst composition, comprising:
   an inert hydrocarbon solvent, having dissolved therein
      a titanate of the formula Ti(OR)$_4$ wherein each R is the same or different, and is a hydrocarbon residue, and
      an organic aluminum compound; and
   a catalyst modifier selected from a silicate, a silazane, a fluorinated hydrocarbon, or a combination thereof;
   wherein a molar ratio of the organic aluminum compound to any alkene present in the catalyst composition is greater than one.

2. The catalyst composition of claim 1, wherein the titanate is pre-treated with the inert hydrocarbon solvent in the absence of the organic aluminum compound.

3. The catalyst composition of claim 1, wherein the inert hydrocarbon solvent is an alkane or an aromatic hydrocarbon.

4. The catalyst composition of claim 1, wherein the ratio of aluminum to titanium in the catalyst composition is about 1:1 to about 40:1.

5. The catalyst composition according to claim 1, wherein one or more of the following conditions is met:
   the content of compounds comprising a carbon chain of more than 20 carbon atoms is less than 0.1 wt. %, based on the total weight of the catalyst composition; or
   the content of a polymer comprising 5 or more repeat units is less than 0.1 wt. %, based on the total weight of the catalyst composition.

6. The catalyst composition according to claim 1, wherein the titanate is Ti(O-butyl)$_4$, Ti(O-n-alkyl)$_4$, Ti(O-n-butyl)$_4$, or a combination thereof; and
   the organic aluminum compound is of the formula Al$_n$R$_{3n}$, wherein n is 1 or 2 and each R is the same or different, and is hydrogen, a hydrocarbon residue, or halogen.

7. A process for the preparation of a catalyst composition, comprising:
   combining the components of claim 1.

8. The process according to claim 7, comprising:
   pretreating the titanate, the catalyst modifier, and optionally a catalyst additive with the inert hydrocarbon solvent; and
   combining the pre-treated titanate with the organic aluminum compound.

9. The process of claim 7, wherein not more than 0.1% wt. % of the alkene is present in the catalyst composition during the process.

10. The process of claim 8, wherein the pre-treating of the titanate comprises dissolving the titanate and the catalyst modifier in the inert hydrocarbon solvent in the absence of the organic aluminum compound.

11. The process of claim 7, comprising:
   combining the organic aluminum compound and the inert hydrocarbon solvent to provide an organic aluminum solution; and
   combining the organic aluminum solution with the titanate and the catalyst modifier.

12. A process for the preparation of an α-olefin, comprising
   contacting an alkene with the catalyst composition according to claim 1 in a liquid phase and under conditions effective to form the α-olefin.

13. The process of claim 12, wherein the alkene is ethene and the α-olefin is 1-butene.

14. The process of claim 12, wherein the contacting is in a homogeneous liquid phase.

15. The process of to claim 12, wherein the liquid phase comprises the α-olefin.

16. The process of claim 12, wherein the conditions comprise at least one of
   a pressure of about 1 to about 120 bar, or
   a temperature of about 30 to about 150° C.

17. The process of claim 12, further comprising:
   reacting the α-olefin to provide the downstream product, wherein the downstream product is a homopolymer or copolymer comprising units derived from the α-olefin.

18. The process according to claim 17, further comprising shaping the downstream product to provide an article.

* * * * *